US00PP16053P2

(12) United States Plant Patent
Dümmen

(10) Patent No.: US PP16,053 P2
(45) Date of Patent: Oct. 18, 2005

(54) ***BEGONIA* PLANT NAMED 'BBEVA'**

(50) Latin Name: *Begonia×hiemalis*
Varietal Denomination: Bbeva

(75) Inventor: Tobias Gunter Dümmen, Rheinberg (DE)

(73) Assignee: Begonia Breeders Association B.V., Aalsmeer (NL)

( * ) Notice: Subject to any disclaimer, the term of this patent is extended or adjusted under 35 U.S.C. 154(b) by 0 days.

(21) Appl. No.: 10/859,495

(22) Filed: Jun. 1, 2004

(51) Int. Cl.[7] ..... A01H 5/00
(52) U.S. Cl. ..... Plt./344
(58) Field of Search ..... Plt./344, 343

(56) References Cited

U.S. PATENT DOCUMENTS

PP4,127 P * 10/1977 Joachim-Rohde ..... Plt./344
PP10,805 P * 2/1999 Man ..... Plt./344

OTHER PUBLICATIONS

UPOV ROM GTITM Computer Database, GTI Jouve Retrieval Software 2004/06 Citations for 'Bbeva'.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Begonia* plant named 'Bbeva', characterized by its compact, upright and mounded plant habit; double flowers with yellow orange and orange bi-colored tepals; and excellent flower longevity.

1 Drawing Sheet

Botanical classification: *Begonia×hiemalis*.
Cultivar designation: 'Bbeva'.

BACKGROUND OF THE INVENTION

The present Invention relates to a new and distinct cultivar of *Begonia* plant, botanically known as *Begonia×hiemalis*, commercially known as Elatior *Begonia*, and hereinafter referred to by the name 'Bbeva'.

The new *Begonia* was discovered and selected by the Inventor in a controlled environment in Aalsmeer, The Netherlands in April, 1999, as a naturally-occurring whole plant mutation of *Begonia×hiemalis* 'Julie', disclosed in U.S. Plant Pat. No. 10,805. The new *Begonia* was observed as a single plant in a group of flowering plants of the parent cultivar.

Asexual reproduction of the new *Begonia* by cuttings in a controlled environment in Aalsmeer, The Netherlands since 1999, has shown that the unique features of this new *Begonia* are stable and reproduced true to type in successive generations.

SUMMARY OF THE INVENTION

The cultivar 'Bbeva' has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Bbeva'. These characteristics in combination distinguish 'Bbeva' as a new and distinct *Begonia:*

1. Compact, upright and mounded plant habit.
2. Double flowers with yellow orange and orange bi-colored tepals.
3. Excellent flower longevity.

Plants of the new *Begonia* are most similar to plants of the parent, the cultivar Julie. Plants of the new '*Begonia*' differ primarily from plants of the cultivar Julie in flower color as tepals of plants of the cultivar Bbeva are yellow orange and orange bi-colored whereas tepals of plants of the cultivar Julie are yellow and red bi-colored in color.

BRIEF DESCRIPTION OF THE PHOTOGRAPH

The accompanying colored photograph illustrates the overall appearance of the new *Begonia*, showing the colors as true as it is reasonably possible to obtain in colored reproductions of this type. Colors in the photograph may differ slightly from the color values cited in the detailed botanical description which accurately describe the colors of the new *Begonia*. The photograph comprises a side perspective view of a typical flowering plant of 'Bbeva'.

DETAILED BOTANICAL DESCRIPTION

In the following description, color references are made to The Royal Horticultural Society Colour Chart, 1995 Edition, except where general terms of ordinary dictionary significance are used. The aforementioned photograph and following observations and measurements describe plants grown in Aalsmeer, The Netherlands during the spring and summer, and grown under conditions typical of commercial practice in a glass-covered greenhouse. During the production of the plants, day and night temperatures ranged from 15 to 20° C. and light levels were about 18,000 lux. Plants used for the photograph and the description were grown in 13-cm containers and were about three months old when the photograph and description were taken.

Botanical classification: *Begonia×hiemalis* cultivar Bbeva.
Commercial classification: Elatior *Begonia*.
Parentage: Naturally-occurring whole plant mutation of *Begonia×hiemalis* cultivar Julie, disclosed in U.S. Plant Pat. No. 10,805.

Propagation:

*Type.*—By cuttings.

*Time to initiate roots.*—About two weeks at temperatures of 20° C.

*Time to develop roots.*—About five weeks at temperatures of 20° C.

*Root description.*—Fine, fibrous and well-branched. Plants of the new *Begonia* have not been observed to form tubers.

Plant description:

*Plant form and habit.*—Compact, upright and mounded plant habit; freely branching with about five or six basal branches per plant. Moderately vigorous. Vegetative shoots are formed at basal nodes and flowering shoots are formed at upper nodes.

*Plant height.*—About 20 cm.

*Plant width.*—About 20 to 25 cm.

*Leaves.*—Arrangement: Alternate, simple. Length: About 9 cm. Width: About 6 to 7 cm. Shape: Ovate; asymmetrical. Apex: Acuminate. Base: Oblique. Margin: Doubly crenate. Texture, upper and lower surfaces: Glabrous, smooth; leathery. Venation pattern: Palmate. Color: Developing and fully expanded leaves, upper surface: Close to 131A. Developing and fully expanded leaves, lower surface: Close to 138B. Venation, upper surface: Close to 137A. Venation, lower surface: Close to 137C. Petiole length: About 4 to 6 cm. Petiole diameter: About 4 mm. Petiole color, upper and lower surfaces: Close to 137A. Stipule quantity: Two per leaf. Stipule size: About 1 cm by 1 cm. Stipule texture, upper and lower surfaces: Smooth, glabrous. Stipule color, upper and lower surfaces: Close to 137C.

Flower description:

*Flowering habit.*—Double flowers with about 10 to 12 tepals per flower; flowers arranged in axillary cymes. Numerous cymes in flower simultaneously; about 25 to 30 open flowers per plant. Flowers positioned above and beyond the foliage. Flowers not fragrant.

*Natural flowering season.*—Under natural daylight conditions, plants flower from spring until the fall. Flower initiation and development is induced by long day/short night conditions. Flowering continuous under photoinductive conditions.

*Flower longevity.*—Individual flowers last about four to five weeks on the plant.

*Flowers.*—Shape: Oval; double. Orientation: Flat to cupped. Diameter: About 4 to 5 cm. Depth (height): About 1 cm.

*Flower buds.*—Length: About 1 to 1.5 cm. Diameter: About 2 cm. Color: Close to 22D.

*Tepals.*—Arrangement: Rosette. Shape: Obovate to rounded. Apex: Rounded. Base: Obtuse. Margin: Entire. Length: About 2 to 3 cm. Width: About 3 to 4 cm. Texture, upper and lower surfaces: Smooth, glabrous. Color: When opening, upper surface: 21B. When opening, lower surface: 22D. Fully opened, upper surface: 21B; towards the margins, 30C. Fully opened, lower surface: 22D.

*Flower bracts.*—Quantity: Two per flower. Arrangement: Opposite. Length: About 1 cm. Width: About 1 cm. Shape: Rounded. Apex: Rounded. Base: Cuneate. Margin: Entire. Texture, upper and lower surfaces: Smooth, glabrous. Color, upper and lower surfaces: 146D.

*Peduncles.*—Angle: About 30 to 45° from vertical. Length: About 4 to 5 cm. Diameter: About 3 to 4 mm. Strength: Strong. Texture: Smooth. Color: Close to 146D.

*Pedicels.*—Angle: About 30 to 45° from vertical. Length: About 2 to 3 cm. Diameter: About 2 to 3 mm. Strength: Strong. Texture: Smooth. Color: Close to 21B.

*Reproductive organs.*—Stamens: None observed. Pistils: None observed.

*Seed/fruit.*—Seed and fruit production has not been observed as reproductive organs are not formed.

Disease/pest resistance: Plants of the new *Begonia* have been observed to be resistant to Powdery Mildew. Plants of the new *Begonia* have not been observed to be resistant to pests and other pathogens common to *Begonia*.

It is claimed:

1. A new and distinct cultivar of *Begonia* plant named 'Bbeva', as illustrated and described.

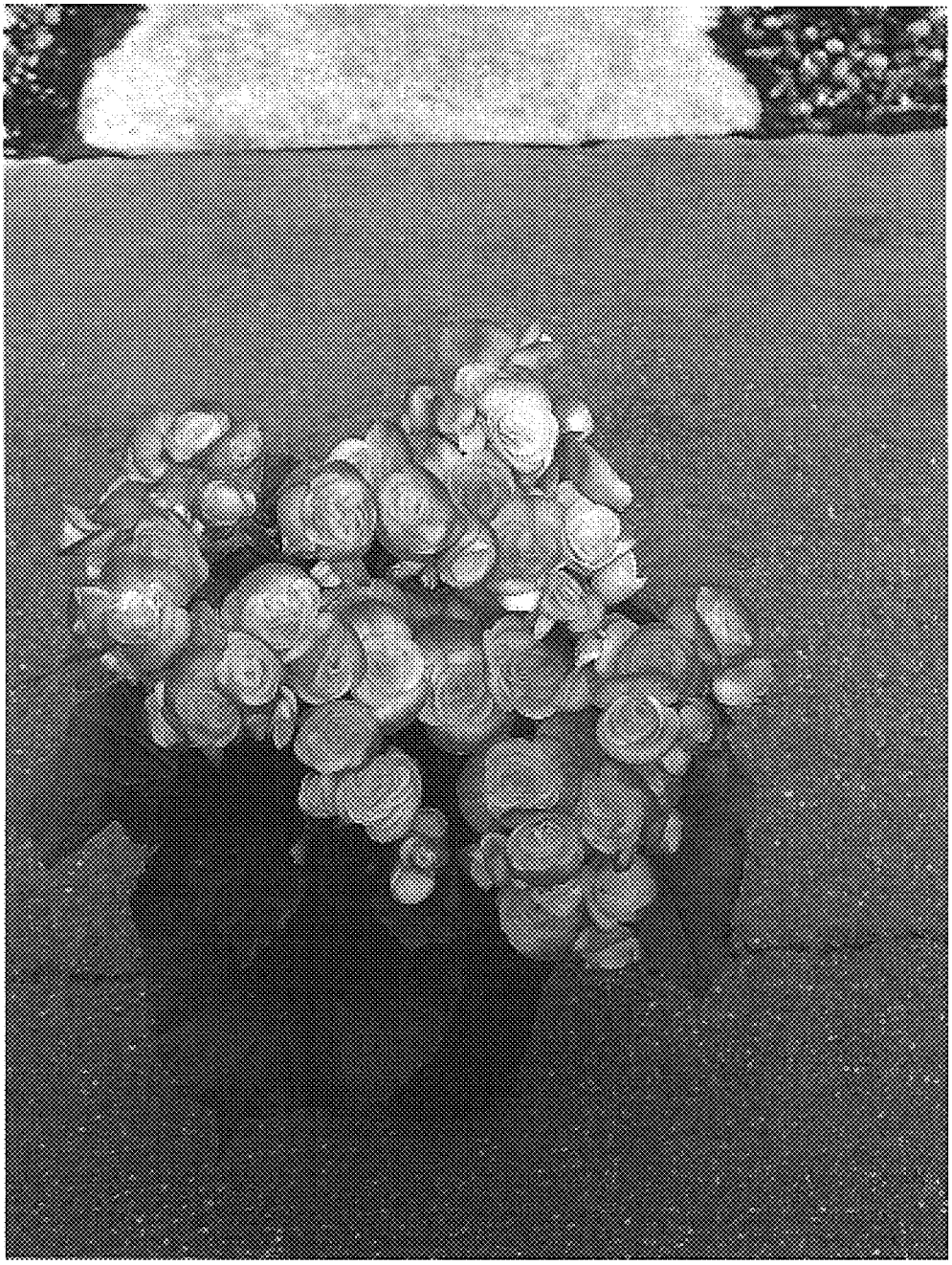

* * * * *